United States Patent [19]
Greenberg

[11] Patent Number: 6,096,275
[45] Date of Patent: Aug. 1, 2000

[54] BIOLOGICAL FLUID TESTING DEVICE

[75] Inventor: Robert C Greenberg, Payson, Ariz.

[73] Assignee: Biological Technologies International, Inc., Payson, Ariz.

[21] Appl. No.: 09/070,996

[22] Filed: May 1, 1998

[51] Int. Cl.$^7$ .......................... G01N 27/07; G01N 27/27; G01N 27/28; G01N 27/38

[52] U.S. Cl. .................... 422/82.02; 422/82.01; 422/82.03; 422/103; 204/409; 204/412; 204/416

[58] Field of Search ..................... 204/409, 416, 204/412, 418, 419; 422/82.02, 82.03, 82.01, 103

[56] References Cited

U.S. PATENT DOCUMENTS

| | | | |
|---|---|---|---|
| 2,886,711 | 5/1959 | Vincent | 204/412 X |
| 2,886,771 | 5/1959 | Vincent . | |
| 3,654,113 | 4/1972 | Bochinski . | |
| 4,206,027 | 6/1980 | Schindler et al. | 204/412 X |
| 4,218,197 | 8/1980 | Meyer et al. | 204/402 X |
| 4,318,884 | 3/1982 | Suzuki | 204/409 X |
| 4,686,011 | 8/1987 | Jackle . | |
| 4,734,184 | 3/1988 | Burledigh et al. . | |
| 4,758,325 | 7/1988 | Kanno et al. . | |
| 4,786,394 | 11/1988 | Enzer et al. . | |
| 4,808,930 | 2/1989 | Kaiser . | |
| 4,844,887 | 7/1989 | Galle et al. . | |
| 4,871,439 | 10/1989 | Enzer et al. . | |
| 4,935,117 | 6/1990 | Uematsu et al. . | |
| 5,046,496 | 9/1991 | Betts et al. . | |
| 5,145,565 | 9/1992 | Kater et al. . | |
| 5,441,049 | 8/1995 | Masano . | |
| 5,520,787 | 5/1996 | Hannagan et al. . | |

FOREIGN PATENT DOCUMENTS

| | | |
|---|---|---|
| 59-100852 | 6/1984 | Japan . |
| 59-178353 | 10/1984 | Japan . |
| 60-1547 | 1/1985 | Japan . |
| 61-164147 | 7/1986 | Japan . |
| 61-176846 | 8/1986 | Japan . |

OTHER PUBLICATIONS

Advertising and User's Manual for Earlier Version of Machine entitled "Introducing the BTA S–1000" No date available.

Primary Examiner—Jill Warden
Assistant Examiner—John S. Starsiak, Jr.
Attorney, Agent, or Firm—Frank J. McGue

[57] ABSTRACT

A device for testing body fluids is disclosed, the device comprising an electrode body having an enclosed flow chamber extending longitudinally therethrough. A valve assembly is in liquid communication with the flow chamber and also detachably mounts a syringe thereon. The valve assembly provides liquid communication between a syringe mounted thereon and the flow chamber. A plurality of electrode cells is detachably mounted to the electrode body and is in liquid communication with the flow chamber. The plurality of electrode cells measures electrical resistivity, $rH_2$, and pH. A circuit electrically connects the plurality of electrodes to an interface providing data output and command input.

17 Claims, 3 Drawing Sheets

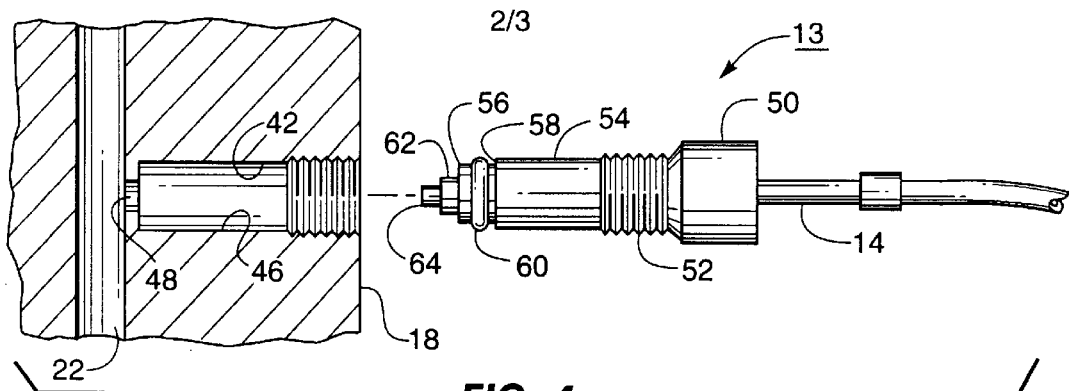
FIG. 4.
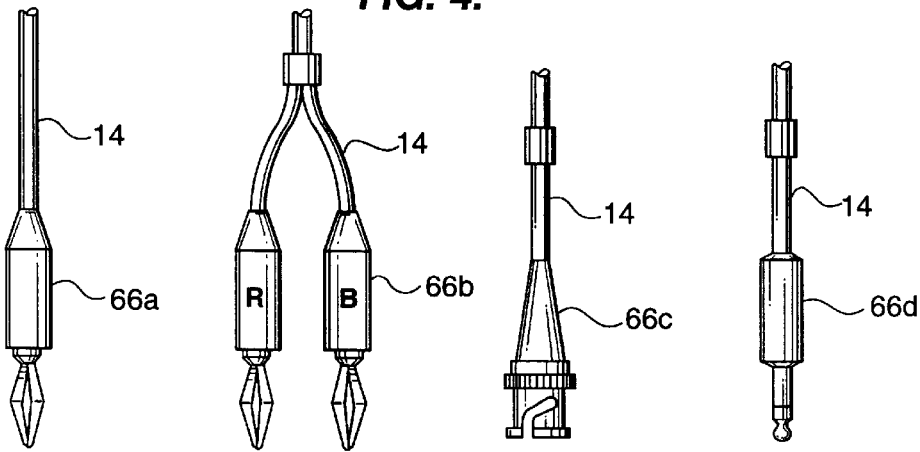
FIG. 5A.  FIG. 5B.  FIG. 5C.  FIG. 5D.
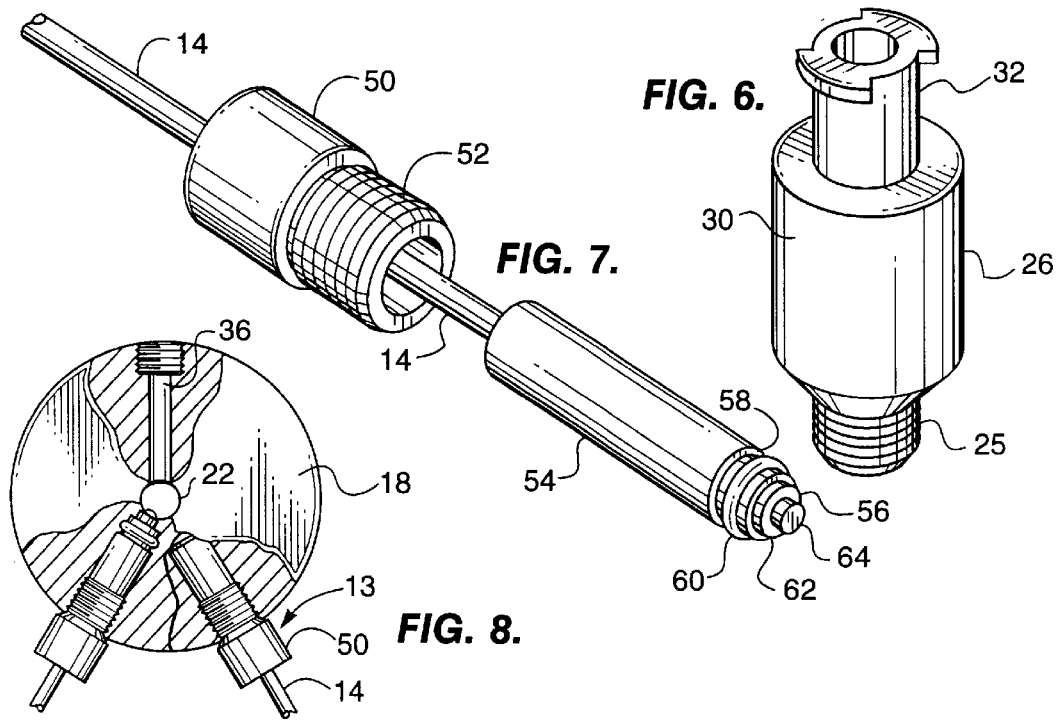
FIG. 6.
FIG. 7.
FIG. 8.

BIOLOGICAL FLUID TESTING DEVICE

TECHNICAL FIELD

This invention relates to the field of devices for testing biological fluids, and, more particularly, to testing urine, blood, saliva or other body fluids for pH, oxidation-reduction potential ($rH_2$) and resistivity to assess the internal biological environment of an individual.

BACKGROUND OF THE INVENTION

The assessment of the internal biological environment of a patient has its beginnings in Europe and is derived from clinical research performed by Louis Claude Vincent. Professor Vincent believed that the key to healing the body was evaluating the biochemistry of a patient. Professor Vincent spent years gathering and evaluating human clinical data which persuaded him that the building blocks of life, to wit, amino acids, enzymes, molecules and atoms found within body fluids provided vital data about the way that particular body was actually functioning. By monitoring the values of pH, oxidation-reduction potential (hereinafter "redox") and resistivity of these body fluids and making changes thereto when necessary, health and vitality could be established in a patient that assisted the patient in naturally fending off illness and disease.

Many fields of medicine simply examine, isolate or treat one particular system or part of a body. In contrast, the assessment of the internal biological environment requires clinical monitoring of the entire body. The goal is to understand the elements within a given patient's chemistry and prescribe the exact form of treatment to allow that patient to regain and maintain a healthy internal biochemical environment. Doing so at the chemical level translates, in time, to vitality and health to every cell, tissue, organ and gland within a patient's body. Since every human body is unique, every ailment must be treated in the context of that particular body. Even patients that display similar conditions such as arthritis or pre-menstrual syndrome may present internal biological environments that differ significantly thus requiring significantly different treatment plans.

Many patients who initially undergo the internal biological environment assessment present reports of normal laboratory results yet display symptoms of illness both subjective and objective. The testing of the internal biological environment may yield data which points to subtle yet potent influences such as parasites, viruses, fungi pollutants, zenobiotics, invasive micro-organisms, free radicals, inadequate vitamins and minerals, an insufficiency of oxygen or an inability to excrete carbon dioxide properly which point to the underlying cause of the patient's illness. However, most standard laboratory tests are inadequate for detecting or measuring such data.

The assessment of a patient's internal biological environment preferably uses that patient's urine, venous blood, and saliva. The patient will undergo a 12–14 hour fast and avoid the use of toothpaste, mouthwash or lipstick which can alter the chemistry of the mouth (saliva). The patient will need to collect his or her first morning urine as a sample. Small amounts (1.5 mL) of venous blood and saliva are collected in the office performing the assessment.

The fluids are tested for pH which is essentially an analytical measurement of the activity and potential energetics of the hydrogen ion. pH is related to the hydrogen ion concentration by the equation:

$$pH = \log(1/H^+Conc.) = -\log H^+Conc.$$

When expressed as shown, the concentrations can be placed on the classic pH scale of 0 to 14.4. When the $H^+$ concentration increases, the pH decreases creating a condition known as acidosis whereas when the $H^+$ concentration decreases, the pH increases creating a condition known as alkalosis. The terms acidosis and alkalosis refer to the relative concentrations of an acid versus a base. Excess acid in relation to a base results in acidosis while excess base in relation to acid results in alkalosis.

There are a number of acids and bases that function in a biological capability. The acids include, but are not limited to, hydrochloric acid, carbonic acid, acetic acid, uric acid, phosphoric acid and nitric acid. The bases include, but are not limited to, bicarbonate ions, sodium bicarbonate, sodium phosphate, special inter-cellular proteins and hemoglobin.

A number of vital pH measurements have been made on various body fluids which define the definitive biochemical balance within a human body. A chart is provided which details the pH measurement ranges for various body fluids:

| TISSUE OR FLUID | pH RANGE |
| --- | --- |
| Saliva | 6.0–7.0 |
| Gastric secretion | 1.0–3.5 |
| Pancreatic secretion | 8.0–8.3 |
| Bile | 7.8 |
| Small intestinal secretion | 7.5–8.0 |
| Urine | 4.5–8.0 |
| Arterial blood | 7.4–7.45 |
| Capillary blood | 7.35–7.4 |
| Venous blood | 7.3–7.35 |

As shown, the pH ranges for the listed fluids falls within a relatively narrow range. If the pH values vary outside this range, cellular function diminishes which may lead to death of the organism Consequently, the body has developed numerous and elaborate systems known as acid-base buffer systems, to regulate and maintain the above pH levels.

In general, a buffer is a solution containing two or more chemical compounds which prevent significant alterations in pH regardless of whether an acid or a base is added to the solution. The buffer systems most active in a body are the bicarbonate/carbon dioxide system, the extracellular system which is mainly comprised of the relative concentration of phosphate, the intercellular system (intercellular proteins/hemoglobin) and bone. While these buffer systems are very effective, variances in the pH levels do often occur.

Most often, such variations are the result of the constant bombardment of the body by acids, both from internal metabolic sources as well as exogenous sources. Acids are formed internally as a normal function of cellular metabolism This normal acid production increases during, for example, times of stress and during exercise. The culprit for excess acid production is the oxidation of fats, carbohydrates and proteins.

The typical American adult consumes over 150 milliequivalents (mEQ) of acids. If the body is unable to process this acid, the body must store the acid. The initial area is the interstitial cells or matrix which is the most biologically benign area for acid storage. However, if this area becomes saturated with acid, other areas used for storage are less benign. As the body becomes loaded with acid, metabolism, respiration, and enzyme kinetics are greatly affected, generally leading to pathology. This pathology can effect the digestive, immune and lymphatic systems.

It should be apparent from this abbreviated discussion that a simple, accurate assessment of the varying fluid pH levels can provide valuable information as to the health of the patient being evaluated.

The second factor to properly assess the biological environment is termed oxidation-reduction potential (redox). Redox is a measurement of the ability of the tested system to gain or lose electrons until it reaches a state of equilibrium. A system which donates electrons is considered to be a reducing system while a system which accepts electrons is considered to be an oxidizing system. In living tissue, oxidation-reduction systems can be divided into two types which can occur either simultaneously or consecutively, namely:

1) those in which the oxidized and reduced forms differ solely in the number of electrons, and
2) those in which "hydrogen transfer" occurs.

When a metal electrode is placed into a solution containing a reversible oxidation-reduction system, the electrode will analytically measure the oxidation-reduction potential. The measurement is generally in the range of millivolts and is represented by the letter E. The general equation is:

Reduced substance ⇌ Oxidized substance+electron=$E$

If E is positive, the reaction has a greater tendency to occur in the direction that the arrow is drawn and hence favors the oxidized state. If, however, E is negative, the reaction has a greater chance to occur in the direction opposite the arrow and hence favors the reduced state. Examples of both are presented below:

Na ⇌ Na$^+$+$e^-$=2.71 mV (favors oxidized state)

Ag ⇌ Ag$^+$+$e^-$=−0.80 mV (favors reduced state)

The biological purpose of oxidation and reduction is two fold. First, oxidation and reduction creates high cellular energy in the form of adenosine triphosphate (ATP). Second, oxidation and reduction is used to oxidize or burn up invading pollutants, xenobiotics and some micro-organisms. Failure of the body to accomplish both purposes would quickly deplete the body of the energy needed to function and would result in serious pathology due to the inability of the body to rid itself of invaders.

When body fluids are loaded with electrons and have a negative E value, the potential for life giving reactions is highest. If the E value becomes more positive, the potential is minimized. Thus, assessing the E value provides tangible analytical evidence as to the energetics and life sustaining properties of a body fluid.

In a measurement, instead of E the analytic tool measures a quantity called rH$_2$ which represents the partial pressure of hydrogen on the electrode. rH$_2$ is calculated from the Nernst equation:

$$E=E°+2.3(RT/F)\log(H^+/rH_2)$$

where:

E=oxidation-reduction potential in millivolts
E°=the standard potential occuring when all activities are equal
R=the gas constant
T=temperature in degrees Kelvin
F=Faraday's constant or the number of electrons reacting
solving the equation for rH$_2$ results in a scale in values ranging from 0 to 42 where 0 corresponds to the maximal hydrogen partial pressure of 1 bar and 42 corresponds to the minimal hydrogen pressure of $1\times10^{-42}$ bar. The midpoint of the scale is at rH$_2$=28 at which point the concentration of reductants equals the concentration of oxidants. An rH$_2$ less than 28 represents a reduced state while a value over 28 represents an oxidized state.

The optimal values for pH of biological fluids are well known and clearly documented. However, the optimal values for rH$_2$ are less accessible and subject to some debate. Listed in the following table are values derived from the work of Professor Vincent as well as values corrected as described in the present application:

| FLUID  | Vincent rH$_2$ | Greenberg rH$_2$ |
|--------|----------------|------------------|
| Saliva | 22             | 20.0             |
| Urine  | 24             | 20.6             |
| Blood  | 22             | 21.7             |

The third factor evaluated in an assessment of the internal biological environment of a patient is resistivity which is the ability of a fluid's ability to conduct an electrical current. If an electrical current can pass easily and readily through the fluid, the resistivity is considered to be low. If, however, an electrical current has a great deal of difficulty passing through the solution, then the resistivity is very high. The factor which determines whether or not a fluid is electrically resistant is the relative concentration of electrically conductive ions, which, in the body, are present in the form of mineral salts. If the relative concentration of mineral salts is high, the resistivity will be low and vice versa. Resistivity is a measurement of the concentration of ions in the fluid and is expressed in units of ohms/centimeter.

As in any biological system, a balance or set concentration of mineral salts is essential to allow the system to carry out its many complex chemical reactions. If the concentration deviates from the norm, then the underlying biochemical functions are greatly affected. Excess mineral salts are removed from the body via the kidneys and urine. If the body loses too many salts or does not remove enough salts, the body will become toxic and underlying function will suffer. Osmotic gradients, cellular integrity, chemical reactivity and proper neurological function are all dependent upon proper mineral salt balance. Thus, resistivity provides indications of blood purification, kidney excretion, enzymatic concentration, dietary factors and alkaline reserve potential can be evaluated.

The optimal values for the resistivity of some body fluids were derived by Vincent and are given in the following chart:

| FLUID  | Vincent resistivity |
|--------|---------------------|
| Saliva | 180–220             |
| Urine  | 30–45               |
| Blood  | 190–210             |

To summarize, there exists a strong interrelationship between the values of pH, rH$_2$ and resistivity. All three parameters are necessary to provide an accurate picture of the internal biological environment of a patient. It must be emphasized that measurement and evaluation of the above three parameters do not diagnose any specific pathology or disease. These parameters are guideposts to aid in the overall evaluation of a patient. The purpose of the evaluation is threefold.

First, the evaluation allows the practitioner to document a reference point to determine if a methodology selected for therapeutic purposes is appropriate. Second, the evaluation provides the practitioner with a teaching guide to share with a patient which allows the patient to take an active role in his or her own health care. Lastly, the parameters provide the practitioner with immediate, easily ascertainable information that is irreplaceable in helping to determine the need for specific laboratory assays.

There have been a number of devices similar to the present invention in the prior art. For example, the present inventor has marketed a device known under the name BTA S1000 which used a dip style electrode in an open environment without temperature compensation. The solid pen style electrodes were not removable. The dip style electrodes tended to trap air bubbles which affected the accuracy and repeatability of measurements. The electrodes of the prior device were manufactured of a commercially available Plexiglas® material.

U.S. Pat. No. 2,886,771 entitled "Fluid-Testing Device" which issued on May 12, 1959 to Vincent (whose contributions to the field were discussed above) discloses a device for testing fluids such as blood, urine, spinal fluid and the like for pH, resistivity and redox. There is a thermostat for maintaining a constant temperature. Note FIGS. 5 and 6 where a syringe is used to draw fluids across a series of electrodes.

U.S. Pat. No. 4,786,394 entitled "Apparatus for Chemical Measurements of Blood Characteristics" which issued on Nov. 22, 1988 to Enzer et al. shows an apparatus for measurement of blood characteristics. Blood is routed through a flow chamber having a vertically aligned array of electrodes. The electrodes are in communication with a microprocessor having a display.

U.S. Pat. No. 5,046,496 entitled "Sensor Assembly For Measuring Analytes in Fluids" which issued on Sep. 10, 1991 to Betts et al. discloses another cell in which a syringe draws fluid across a series of electrodes then expels the fluid.

U.S. Pat. No. 4,844,887 entitled "Automatic Analyzing Apparatus" which issued on Jul. 4, 1989 to Galle et al. shows an analyzing apparatus in which fluids are drawn by syringe 179 across electrodes 183. Valve 180 is opened and pump 182 evacuates the fluid to tank 181.

U.S. Pat. No. 4,686,011 entitled "Method for the Protection of and/or Monitoring of Changes in a Reference System in Analytical Measuring Engineering, and Reference System with a Reference Electrode" which issued on Aug. 11, 1987 to Jackle is cited to show that it is known to use a reference electrode.

U.S. Pat. No. 3,654,113 entitled "Programmed Fluid Sampling and Analysis Apparatus" which issued on Nov. 24, 1972 to Bochinski shows a fluid sampling and analysis apparatus utilizing valves 30 and 40 which in one position allow circulation of a fluid and in another position send the fluid to a drain line.

None of the known prior art disclose the combination set forth herein.

SUMMARY OF THE INVENTION

It is an object of this invention to provide an improved apparatus for testing pH, resistivity, $rH_2$, and E (oxidation-reduction potential) directly using easily interchangeable cell components.

It is a further object of this invention to provide an improved apparatus for evaluating the internal biological environment of a patient which provides automatic temperature compensation.

It is still another object of this invention to provide an improved apparatus for evaluating the internal biological environment of a patient which utilizes statistical techniques to ensure goods readings.

Further objects and advantages of the invention will become apparent as the following description proceeds and the features of novelty which characterize this invention will be pointed out with particularity in the claims annexed to and forming a part of this specification.

BRIEF DESCRIPTION OF THE DRAWINGS

The present invention may be more readily described by reference to the accompanying drawings in which:

FIG. 4 is side cross sectional view of the embodiment of FIG. 3 taken along line 4—4;

FIGS. 5A–5D are various embodiments of connectors used to connect the electrodes to the electronics of the present invention;

FIG. 6 is a perspective view of one embodiment of an overflow chamber used in the present invention;

FIG. 7 is an exploded perspective view of one embodiment of an electrode of the present invention;

FIG. 8 is a top cross sectional view of one embodiment of the electrode assembly of the present invention;

DESCRIPTION OF THE PREFERRED EMBODIMENT

Figure 1:
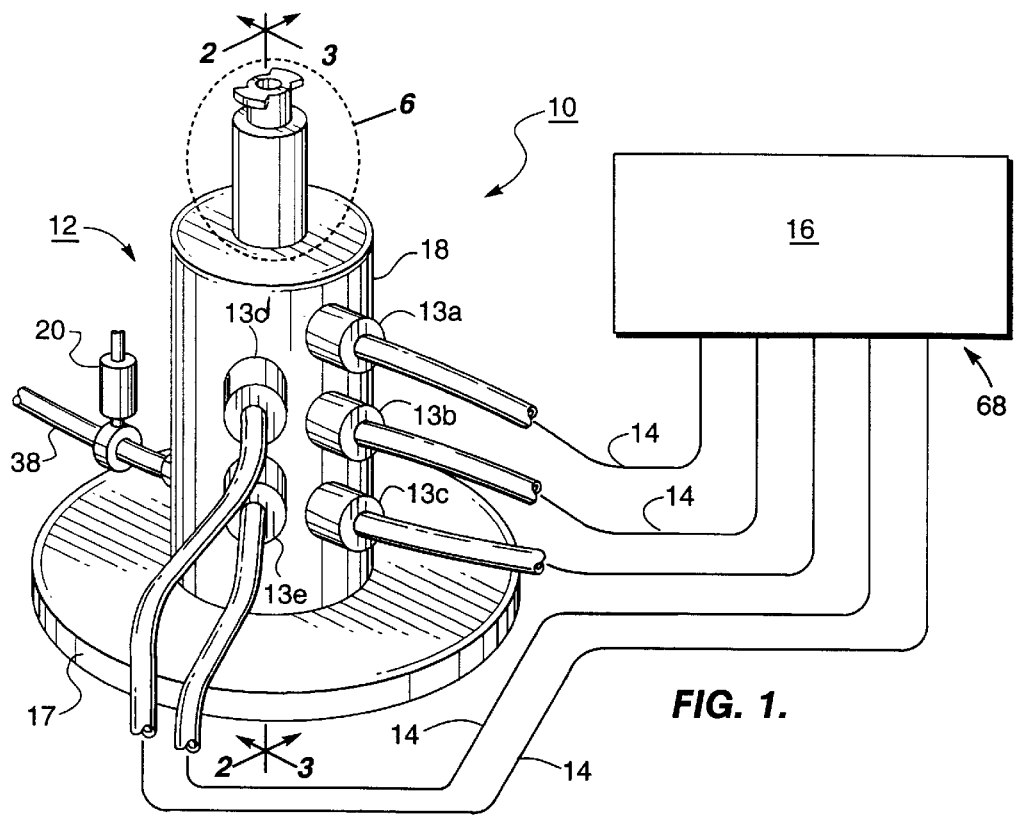
FIG. 1 is a perspective view of an electrode assembly of the present invention.

Referring more particularly to the drawings by characters of reference, FIGS. 1–8 disclose combinations of features of the present invention which constitute various embodiments of a biological fluids testing device 10 comprising an electrode assembly 12 having a plurality of electrode cells 13a–13e in electrical communication via wires 14 with a data acquisition command module 16. Electrode assembly 12 comprises a base 17, an electrode body 18 mounted atop base 17, the plurality of electrode cells 13 extending into body 18 and an electrode valve assembly 20 also extending into body 18 proximate to base 17.

Figures 2, 3:
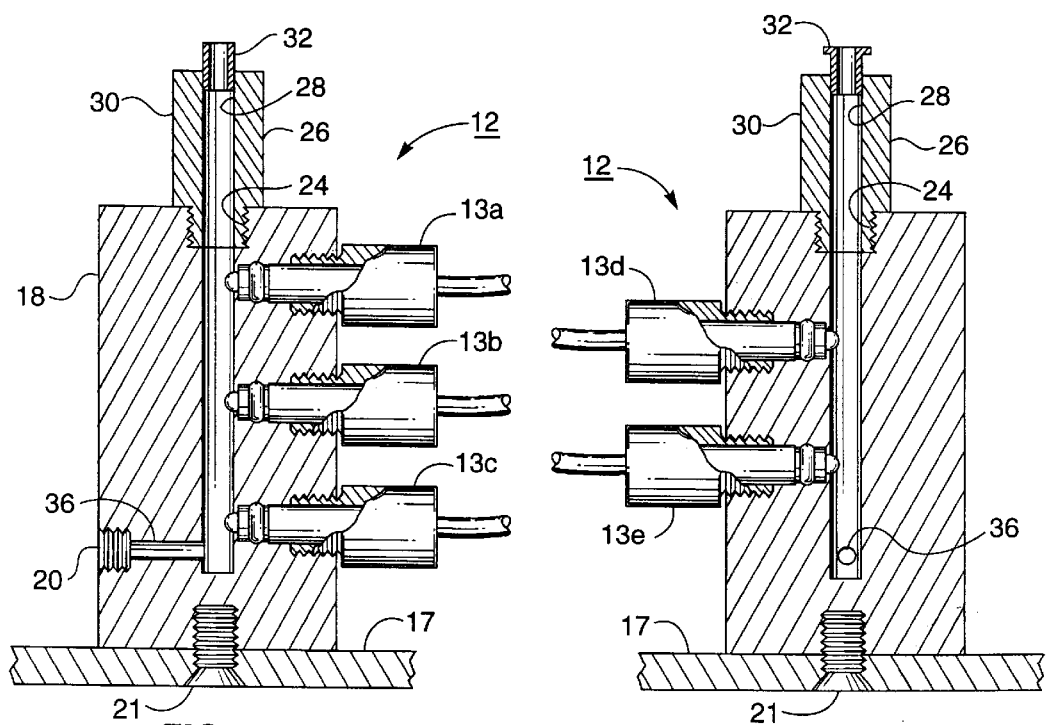
FIG. 2 is a cross sectional side view of the electrode assembly of FIG. 1 taken along line 2—2.
FIG. 3 is a cross sectional side view of the electrode assembly of FIG. 1 taken along line 3—3.

In the illustrated embodiment of FIG. 1, base 17 is a circular plate. However, those skilled in the art will recognize that base 17 can be any shape which provides stability during normal use. Further, as best seen in FIGS. 2 and 3, base 17 is detachably secured to electrode body 18 by screw 21 extending therethrough. However, screw 21 is used as means for securing body 18 to base 17 for purposes of illustration only. Many other means for securing body 18 to base 17, either detachably or permanently, are contemplated as those skilled in the art will recognize.

Extending longitudinally through body 18 and upwardly from base 17 is a cylindrical flow chamber 22. Chamber 22 is closed at its bottom. However, at the top of chamber 22, a threaded bore 24 receives a mating lower threaded portion 25 of an overflow chamber body 26. Overflow chamber body 26 includes an overflow chamber 28, which, when threaded portion 25 is threadedly engaged to threaded bore 24, is in liquid communication with chamber 22. The middle portion 30 of chamber body 26 is preferably transparent to allow visual inspection of the contents of overflow chamber 28.

Mounted atop overflow chamber body 26 is means 32 for detachably receiving a syringe 34. In the illustrated embodiment, such means 32 is a female leur lock available from Shawnee Mfg. Co. of Eminence, Mo. as part no. SMC-1003. The complete overflow chamber body including means 32 is also available from Shawnee Mfg. Co. of Eminence, Mo. under part no. SMC-1002B. Such means 32 provide liquid communication between the interior of syringe 34 and overflow chamber 28. Such means 32 are well known in the art and are not further discussed herein.

As best seen in FIGS. 2 and 3, extending laterally from flow chamber 22 is a valve assembly bore 36 which provides liquid communication between flow chamber 22 and valve assembly 20 through body 18. Valve assembly 20 is, preferably, threadedly mounted to bore 36 though other means for mounting are certainly within the scope of the present invention. Valve assembly 20 is available as part number 6011 from Popper & Sons of New Hyde Park, N.Y.

Figure 9A:
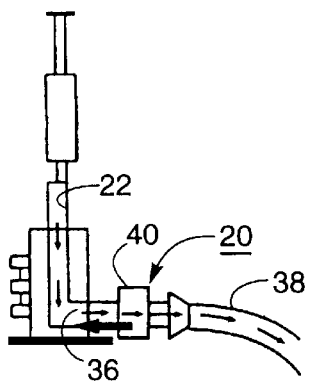
FIGS. 9A–9C provide schematic drawing showing the operation of a valve assembly of the present invention.
Figure 9B:
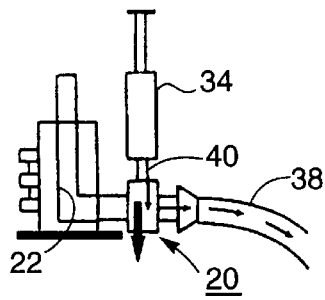
Figure 9C:
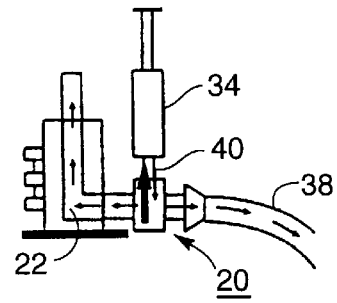

Valve assembly 20 is in liquid communication between the flow chamber 22 via valve assembly bore 36, a drainage line 38 and a second means 40 for detachably mounting a syringe 34 thereon. As best seen in FIGS. 9A–9C, valve assembly 20 includes three valve positions. The first position show in FIG. 9A provides liquid communication between flow chamber 22 and drainage line 38. The second position shown in FIG. 9B provides liquid communication between means 40 and drainage line 38. The third position shown in FIG. 9C provides liquid communication between means 40 and flow chamber 22. The three positions of FIGS. 9A–9C provide for cleaning, calibration and testing functions needed for operation of device 10 as further described below.

A plurality of electrode bores 42 extend laterally from flow chamber 22 to the exterior of body 18. As best seen in FIG. 4, each electrode bore 42 includes an outer female threaded bore 44 abutting the exterior of body 18, a concentric smaller diameter middle bore 46 and a small inner concentric bore 48 abutting flow chamber 22. A bore shoulder 49 separates middle bore portion 46 and inner bore 48.

The corresponding electrode cell 13 comprises an exterior portion 50 abutting a male threaded portion 52 which mates with and engages female threaded portion 44. As best seen in FIG. 7, extending into male threaded portion 52 is a first cylindrical portion 54 which, in turn, abuts a second cylindrical portion 56. A cell shoulder 58 separates first cylindrical portion 54 and second cylindrical portion 56. An O-ring 60 is mounted on second cylindrical portion 56. When electrode cell 13 is mounted within electrode bore 42, O-ring 60 is captured between bore shoulder 49 and cell shoulder 58 to provide a liquid tight seal therebetween.

One key to the present invention is the use of interchangeable electrodes 13 allowing easy repair and replacement of same as needed. In addition, electrodes 13 are now manufactured from an autoclavable material, preferably ULTEM 1000, available from DuPont de Nemours & Co., instead of the former Plexiglas® material of the prior art.

A small inner portion 62 extends through small inner bore 48. Extending from inner portion 62 is an electrode probe 64 which extends into flow chamber 22. Electrode probe 64 is electrical communication with wires 14 extending outwardly from cylindrical portion 54 through exterior portion 50 of each electrode cell 13.

In the presently preferred embodiment, electrode cell 13a is used to measure resistivity, electrode cell 13b is used to measure $rH_2$, 13c is used to measure the temperature, 13d is a reference cell and 13e is used to measure pH. It will be understood by those skilled in the art that the positions of each electrode are solely for purposes of illustration and are not intended to limit the scope of the present invention.

Wires 14 can connect electrodes 13a–13e to data acquisition command module 16 by appropriate connectors. In the presently preferred embodiment, banana plug 66a is used to connect reference electrode 13d, double banana plug 66b is used to connect resistivity electrode 13a, BNC plugs 66c are used to connect the pH and $rH_2$ electrodes 13b and 13e, and subminiature phone plug 66d used to connect temperature electrode 13c. The various connectors are illustrated in FIGS. 5A–5D. It is preferable to have each electrode 13a–13c have a different connector which eliminates the problem of connecting an electrode to the wrong plugin connection on data acquisition command module 16. Such connectors are well known in the art and will not be further discussed herein.

Turning now to the specifics of each electrode, it will be understood that the parameters discussed below are generally, except where noted, matters for engineering design.

Resistivity electrode 13a is calibrated by placing same in a Kcl conductivity standard solution at 10,000 $\mu$S/cm. The reading is calibrated to read 10,000 $\mu$S/cm and the slope is verified to be 2±0.5 cm$^{-1}$.

pH electrode 13b has a range from 0 to 12 pH and is accurate in a temperature range of −5 to 125° C. In a pH 7.00 solution, pH electrode 13b has an output of 0±20 millivolts with a slope of 170 mV between pH 4.01 to pH 7.00. Thus, the pH of a solution is determined by the following equation:

$$pH=4+(3\times mV)/170$$

in which pH=desired number mV=millivolt reading of sensor

Electrode 13b is available as Part No. PH20001 C-03T-B from Analytical Sensors, Inc. of Houston, Tex.

Temperature electrode 13c, preferably, utilizes a 10K$\Omega$ thermistor probe having a response time of 30 seconds to 95% of the final reading. The thermistor is accurate to ±2° C. at room temperature. Electrode 13c is available as Part No. TC0200CA-03T-F2 from Analytical Sensors, Inc.

Temperature electrode 13c is used to provide a temperature correction factor for such values as $rH_2$ which are temperature dependent. The correction factor is given by the following equation:

$$rH_2=2\times\{pH+[(mV+207)/59.2]\}$$

Reference electrode 13d is a ceramic construction which has a reference potential compared to a standard Ag/AgCl/4 M Kcl reference probe of 0±10 mV. Reference electrode 13d is available as part number RF0010CR-3T-E from Analytical Sensors, Inc.

$RH_2$ electrode 13e is a silver probe as opposed to the previously used platinum probes of the prior art. The probes of the prior art were subject to a phenomena known as electrode poisoning. Electrode poisoning is either the chemical absorption of oxygen by the electrode when placed in an oxidizing solution or the chemical absorption of hydrogen when the electrode is placed in a reducing solution. The absorbed oxygen/hydrogen serve as an oxidation/reduction (respectively) reserve which tend to maintain the electrode potential at an elevated/reduced level even when the redox potential has diminished/increased.

To solve the problem of electrode poisoning, $rH_2$ electrode 13e probe is chemically and electrically treated to create a coating by placing it in a 4 molar potassium chloride solution and running a nine volt current therethrough for five minutes while so immersed. The silver and the potassium chloride interact under such conditions to form a chemical layer impervious to electrode poisoning contamination from biological fluids. $RH_2$ electrode 13e will read 86±15 mV in a pH 7.00 solution (saturated with quinhydrone and 252±15 mV in a pH 4.00 solution (also saturated with quinhydrone). $RH_2$ electrodes 13e are available as part no. OR2000CA-03T-B from Analytical Sensors, Inc.

The mV reading obtained from the $rH_2$ electrode is in millivolts and corresponds to the oxidation-reduction potential (ORP) of the solution. To obtain an $rH_2$ value, the following equation is employed:

$$rH_2 = 2 \times \{pH + [(ORP+207)/59.2]\}$$

The temperature corrections in use and the use of the silver electrode 13e of the present invention has resulted in adjustments to the standard nominal ranges for $rH_2$ values as shown in the chart reprinted above in the Background of the Invention. Electrode poisoning was not well understood in Professor Vincent's day, thus, his nominal values require some adjustment due to the newer understanding of this phenomena.

If the $rH_2$ of water is to be measured, a standard platinum electrode 13e is employed. The platinum electrode has the same readings as the silver probe discussed above. $rH_2$ platinum electrode 13e is available as part number OR1000CA-03T-B available from Analytical Sensors, Inc.

To test a particular biological fluid, valve assembly 20 is placed in the third position illustrated in FIG. 9C to allow liquid communication between second means 40 and flow chamber 22. Syringe 34 containing the fluid to be tested is attached to second means 40 and the fluid contained therein (approximately 3–5 ccs) is injected into flow chamber 22. Enough biological fluid is injected to fill approximately ¾ full overflow chamber 28. The testing is the run using the electrodes 13.

With regard to the pH and $rH_2$ readings, a special statistical sampling is taken. Specifically, 10 readings are taken and a standard deviation is calculated from same. If the standard deviation is less than, the reading is accepted. If the standard deviation is outside this parameter, the system automatically takes an eleventh reading, drops the first and recalculates the standard deviation. The process continues for 50 samples or until the data stabilizes within the 0.02 mV standard deviation. If the value still does not meet the standard deviation after fifty samples, the test is aborted and the user warned of a variance.

To clean between biological fluids, valve assembly 20 is placed in the first position illustrated in FIG. 9A allowing liquid communication between flow chamber 22 and drainage line 38. Syringe 34 filled with tap water is attached to first means 32. By pumping syringe 34, a powerful rinsing action is created within flow chamber 22. Syringe 34, or a second syringe, is filled with an electrode cleaning solution, preferably sodium hypochlorite, which is attached to first means 32 and pumped as previously described. The procedure is repeated using distilled water and finally an air filled syringe 34 is employed to force any remaining fluids from flow chamber 22.

Valve assembly 20 is placed in the second position illustrated in FIG. 9B which provides liquid communication between second means 40 and drainage line 38. Syringes 34 filled with tap water, electrode cleaning solution, distilled water and finally air are sequentially attached to second means 40 and the pumping action used to thoroughly clean and dry valve assembly 20.

Those skilled in the art will recognize that calibration between calibration is a similar procedure as above except that instead of a biological fluid being used, a solution having known values is employed as a calibration fluid. In addition, cleaning between calibrations generally only requires the use of a distilled water flush.

Figure 10:
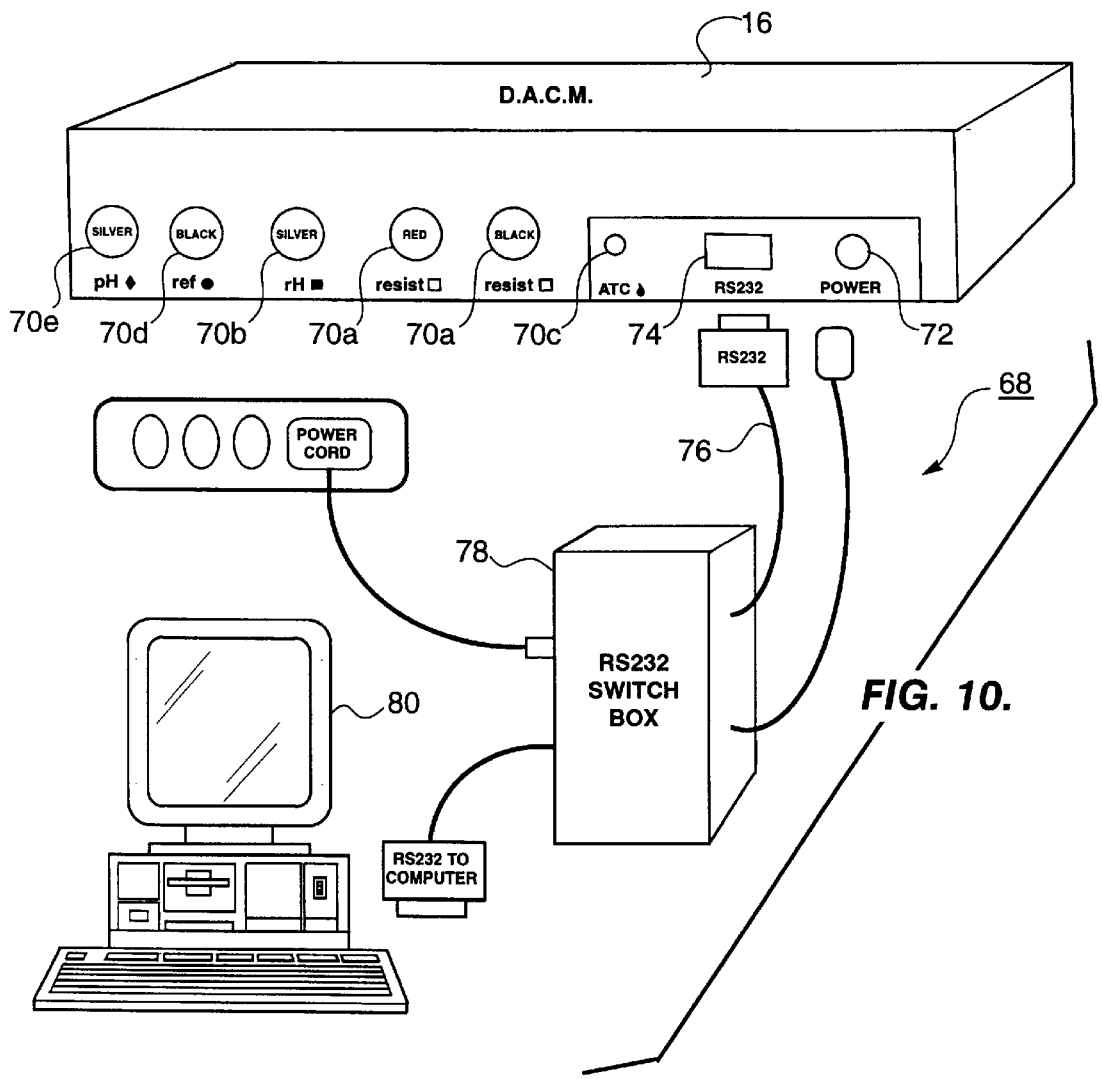
FIG. 10 is a schematic showing the connections between one embodiment of the entire system.

Turning now to FIGS. 1 and 10, a complete operating system 68 comprising wires 14 electrically connecting electrodes 13 to data acquisition command module 16 providing data output and command input is illustrated. As previously discussed, electrodes 13a–13e are connected to ports 70a–70e, respectively, of data acquisition command module 16 by connectors 66. Power is supplied to data acquisition command module 16 via power connector 72. As best seen in FIG. 10, data acquisition command module 16 takes the incoming signals from electrodes 13 and converts those signals via the formulae previously described to the values desired. These values are forwarded via RS232 port 74, RS232 switch box 78 to a computer 80 for appropriate display. Instructions from a user are entered into computer 80 and, in reverse fashion, forwarded to data acquisition command module 16 via RS232 switch box 78. Such instructions include, but are not limited to, ordering data acquisition command module 16 to take readings from electrodes 13 for data or for calibration purposes.

Although only certain embodiments have been illustrated and described, it will be apparent to those skilled in the art that various changes and modifications may be made therein without departing from the spirit of the invention or from the scope of the appended claims. For example, the data acquisition module, the computer and the RS232 unit could all be incorporated into a single, stand alone, integrated unit as those skilled in the art will recognize.

What is claimed is:

1. A device for testing body fluids, the device comprising:
an electrode body having an enclosed flow chamber extending longitudinally therethrough,
a valve assembly in liquid communication with the flow chamber and a means for detachably mounting a syringe thereon, the valve assembly providing liquid communication between a syringe mounted thereon and the flow chamber,
a plurality of electrode cells detachably mounted to the electrode body and in liquid communication with the flow chamber, the plurality of electrode cells including a reference electrode and means for measuring temperature, electrical resistivity, $rH_2$, and pH; and
a plurality of wires corresponding to and electrically connecting the plurality of electrodes to an operating system providing data output and command input.

2. The device of claim 1 further comprising a base, the electrode body being detachably mounted thereon.

3. The device of claim 1 further comprising an overflow chamber body detachably mounted atop the electrode body, the overflow chamber body having an overflow chamber extending therethrough, the overflow chamber being in liquid communication with the flow chamber when the flow chamber body is mounted atop the electrode body.

4. The device of claim 3 wherein the interior of the overflow chamber is visible from the exterior of the overflow chamber body.

5. The device of claim 3 wherein means for detachably receiving a syringe is mounted atop the overflow chamber body, the means providing liquid communication between the overflow chamber and the syringe.

6. The device of claim 1 further comprising a drainage line in liquid communication the valve assembly, the valve assembly further having a valve having three positions, the first position providing liquid communication between the flow chamber and the drainage line, the second position providing liquid communication between a syringe mounted thereon and the drainage line, the third position providing liquid communication between a syringe mounted thereon and the flow chamber.

7. The device of claim 1 wherein mean for measuring pH comprise a pH electrode, the output of the electrode being in millivolts, the interface means calculating the pH from the millivolt output.

8. The device of claim 7 wherein the pH is calculated from the millivolt output by the following formula:

$$pH=4+(3 \times mV)/170.$$

9. The device of claim 1 wherein means for measuring $rH_2$ comprises an $rH_2$ electrode, the output of the electrode being in millivolts, the interface means calculating the $rH_2$ from the millivolt output.

10. The device of claim 9 wherein the $rH_2$ is calculated from the millivolt output by the following formula:

$$rH_2=2 \times \{pH+[(mV+207)/59.2]\}.$$

11. The device of claim 9 wherein the $rH_2$ electrode is a silver probe.

12. The device of claim 11 wherein the silver probe is coated by immersing the probe into a 4 molar potassium chloride solution and providing a nine volt potential therethrough for five minutes.

13. The device of claim 1 wherein the operating system comprises a data acquisition command module in electrical communication with a computer.

14. The device of claim 13 wherein the data acquisition command module and the computer are integral.

15. A device for testing body fluids, the device comprising:

a base, an electrode body mounted atop the base, the electrode body having an enclosed flow chamber extending longitudinally therethrough, an overflow chamber body detachably mounted atop the electrode body, the overflow chamber body having an overflow chamber extending therethrough, the overflow chamber being in liquid communication with the flow chamber when the flow chamber body is mounted atop the electrode body, the overflow chamber body having means for detachably receiving a syringe is mounted atop the overflow chamber body, the means providing liquid communication between the overflow chamber and the syringe, the interior of the overflow chamber being visible from the exterior of the overflow chamber body;

a valve assembly in liquid communication with the flow chamber and a means for detachably mounting a syringe on the valve assembly, the valve assembly providing liquid communication between a syringe mounted thereon and the flow chamber, a drainage line in liquid communication the valve assembly, the valve assembly further having a valve having three positions, the first position providing liquid communication between the flow chamber and the drainage line, the second position providing liquid communication between a syringe mounted thereon and the drainage line, the third position providing liquid communication between a syringe mounted on the valve assembly and the flow chamber, a plurality of electrode cells detachably mounted to the electrode body and in liquid communication with the flow chamber, the plurality of electrode cells including:

a reference electrode, an electrode for measuring temperature, an electrode for measuring electrical resistivity, an electrode for measuring pH, the pH electrode output being in millivolts and the output being converted to pH by the formula $pH=4+(3 \times mV)/170$;

an electrode for measuring $rH_2$, the $rH_2$ electrode output being in millivolts and the output being converted to rH2 by the formula $rH_2=2 \times \{pH+[(mV+207)/59.2$ the $rH_2$ electrode being a silver probe, the silver probe being coated by immersing the probe into a 4 molar potassium chloride solution and providing a nine volt potential therethrough for five minutes; and a plurality of wires corresponding to and electrically connecting the plurality of electrodes to an operating system providing data output and command input.

16. The device of claim 15 wherein the operating system and the wires are integral.

17. A device for testing body fluids, the device comprising:

an electrode body having an enclosed flow chamber extending longitudinally therethrough, an overflow chamber body detachably mounted atop the electrode body, the overflow chamber body having an overflow chamber extending therethrough, the overflow chamber being in liquid communication with the flow chamber when the flow chamber body is mounted atop the electrode body;

a valve assembly in liquid communication with the flow chamber and a means for detachably mounting a syringe thereon, the valve assembly providing liquid communication between a syringe mounted thereon and the flow chamber, a plurality of electrode cells detachably mounted to the electrode body and in liquid communication with the flow chamber, the plurality of electrode cells including means for measuring electrical resistivity, $rH_2$, and pH; and a plurality of wires corresponding to and electrically connecting the plurality of electrodes to an operating system providing data output and command input.

* * * * *